United States Patent [19]

Sanden et al.

[11] Patent Number: 4,803,887

[45] Date of Patent: Feb. 14, 1989

[54] FLOW-METERING SYSTEM FOR MILK-COLLECTING VEHICLE

[75] Inventors: Ulrich-Christian Sanden, Hildesheim; Manfred Kaune, Schellerten, both of Fed. Rep. of Germany

[73] Assignee: Diessel GmbH & Co., Hildesheim-Bavenstedt, Fed. Rep. of Germany

[21] Appl. No.: 286

[22] Filed: Jan. 2, 1987

[51] Int. Cl.$^4$ .............................................. G01N 1/10
[52] U.S. Cl. .............................. 73/863.01; 73/864.34
[58] Field of Search ...................... 364/571, 550, 551; 73/863.01, 863.02, 863.03, 863.83, 864.34

[56] References Cited

U.S. PATENT DOCUMENTS 4,484,593 11/1984 Rusell ........................... 73/863.01 X
4,660,422 4/1987 Eads et al. ......................... 73/863.02

Primary Examiner—Jerry W. Myracle
Attorney, Agent, or Firm—Gilbert L. Wells

[57] ABSTRACT

The object of the invention is to so design a flow-meter system for milk-collecting vehicles, that a pump, a pulse-controlled sampling device, an air separator and a flow-meter with pulse generator and display are in series in the operational direction, where a computer is provided in the display for analysis, in that independently of the particular quantity delivered, Automatically always the same amount of sample shall be withdrawn, whereby an adepquate amount of sample shall be available for analysis even for small quantities delivered, and where addiional containers are not needed for large quantities delivered, and where overrunning is avoided. To that end, the invention provides tha tthe quantities of milk delivered by the suppliers the day before shall be stored in the computer and be each correlated to the particular supplier, the same number of pulses being assigned to all previous-day quantities, the quantity-dependent pulse-train of these pulses being computed from the previous-day quantities and being emitted by the flow-meter, so that different previous-day quantities correspond to different delivered-quantity/pulses and where these pulses drive the sampling device.

21 Claims, 3 Drawing Sheets

FLOW-METERING SYSTEM FOR MILK-COLLECTING VEHICLE

BACKGROUND OF THE INVENTION

The invention concerns a flow-metering system for milk-collecting vehicles comprising in operational sequence a pump, a pulse-controlled sampling device, an air separator and a flow-meter with pulse generator and display, a computer being provided for analysis in the display.

In manner known per se, an annular sleeve counter with a corresponding display can be used as a flow meter.

Such flow-meter systems suffer from the difficulty in sampling milk during the in-line metering process, it being already known to use pulse-controlled sampling devices allowing to remove samples of 1 to 3 ml a pulse. In the known equipment, the pulses are emitted by a pulse generator connected to the flowmeter.

In the known equipment, a specified, fixed number of pulses is always assigned to a specific flow quantity. This entails the drawback that for insufficient flow quantities. and hence for pulse numbers which are too low, the samples will be too small, or for large amounts and hence large numbers of pulses the sample vessel fills too rapidly and runs over or additional storage vessels for the tapped sample liquid will be needed.

SUMMARY OF THE INVENTION

The object of the invention is to so design a flow-meter system of the initially cited kind that regardless of the particular flow quantities delivered, always the same amount of samples shall be withdrawn, whereby sufficient sampling is available for small deliveries and as regards large deliveries, additional vessels are not needed and overrunning is avoided.

The invention solves this problem by storing in the computer of the display device the quantities of milk delivered by the suppliers the day before and correlating them to the particular suppliers, always the same number of pulses being assigned to the quantities delivered the day before, the quantity-dependent sequence of these pulses being computed from the quantities of the day before and being released by the flow-meter, whereby various previous-day quantities correspond to different delivered-amounts/pulse and whereby these pulses are fed to the sampling device.

As a result, always the same number of pulses distributed across the flow time of a delivered quantity arrives at the computer, which means that the amount of the sample is kept constant, ie independent of the quantity being delivered. Nevertheless the sampling takes place over the entire flow time and accordingly in this respect the sample contains a cross-section of the composition of the delivered milk.

To that end, the quotient of the previous-day quantity to the amount of the sample is appropriately formed do determine from it the particular delivered quantity assigned to each pulse from the following relation:

$$V_1 = V_V \cdot P_1 / P$$

where
  $V_1$ = quantity delivered/pulse
  $V_V$ = previous-day quantity
  $P$ = amount of the sample
  $P_1$ = amount of sample/pulse.

The pulses from the flow-meter are added in manner known per se at the computer in order that upon reaching a value calculated from the above relation, a pulse fed to the sampling system shall be emitted. For acceptance of the quantity delivered, the particular, supplier number is fed into the computer in appropriate manner, possibly by a coded card and an input unit, whereupon the quantity delivered the day before is assigned to the supplier and from it the resultant delivered-quantity/-pulse is computed.

It was found to be especially appropriate to use 20 pulses for one previous-day quantity.

The particular previous-day quantity from the same supplier can be taken into account for the described application of pulses because the deviations in quantities delivered from day to day are relatively small and therefore negligibly small.

Where the deviations are substantial, the system of the invention allows manual intervention in the sampling process. Where called for, a quantity estimated on the basis of the actual conditions can be fed to the computer in lieu of the stored previous-day quantity.

In addition to the described sampling serving to determine the milk ingredients, the system of the invention is suited in especially advantageous manner to withdraw further samples in the same operational step in order to ascertain the milk's bacteriological condition, for instance in order to carry out germ counts and the like.

To that end the invention provides that after half the flow is completed, that is following a number of pulses corresponding to half the predetermined number of pulses, the sampling device be instructed to withdraw a predetermined additional number of samples in one step.

The additional sampling so withdrawn may correspond approximately to half the total sampling used to determine the ingredients.

It is now possible in this manner to use one and the same system to remove samples both for the determination of the ingedients and simultaneously to determine the bacteriological condition, without such samplings interfering with one another.

Sampling to ascertain the bacteriological condition following a specific flow quantity is known per se because portions of a previous quantity of flow must be prevented from entering the sample. Therefore first there must take place so-to-speak rinsing with that milk of which the bacteriological condition is sought.

To withdraw that sample, appropriately a sample-desk holding the sample containers both for the ingredients and also for the bacterial condition samples and switchable between them is provided and associated to the sampling device.

In the rest position of the sample desk, the sample container for ingredient determination is associated with the discharge segment of the valve of the sampling device, the sampling taking place in the manner described during the entire flow by means of the pulses from the computer. After half the provided pulses have been emitted, the sample desk is switched into a position where the discharge segment is associated with that container holding the sample from which the bacteriological condition shall be ascertained. As stated above, this sample is withdrawn in one step. Thereupon the sample desk is returned to its initial position. The sampling to determine the ingredients is then continued in that position in the manner already described.

In an especially appropriate manner, an adder summing the pulses from the computer is provided for switching the sample desk; this adder feeding a a memory and through it the sample desk the moment the predetermined half number of pulses has been emitted. The sample desk can be switched by a rotary magnet driven by the memory, the valve of the sample withdrawal device being opened after this switching operation by a timer and logic. To prevent opening the valve of the sample withdrawing device during the switching of the sample desk, the timer may be connected in such a manner to the memory and the sampling device that the sampling takes place at a time delay of about a second following the switching of the sample desk, whereby the desk shall be reliably switched over before the valve opens. The sample desk can be returned to its initial position by a spring, while the timer can be used to shut down the rotary magnet.

The switching and return of the sample desk or the termination of its motion also may be implemented by limit switches, or by using the rise in current when the rotary magnet is energized as a control means.

The sample desk may be a U-shaped plate of which the two legs are horizontal, the upper free leg having two openings to receive the sample holders. The lower leg can be connected to the shaft of the rotary-magnet core.

A limit-means for the angular motion of the sample desk also is provided to assure automatic alignment of the receiving openings for the purpose of opening the discharge segment of the valve.

BRIEF DESCRIPTION OF THE DRAWINGS

The invention is described in closer detail below in relation to an illustrative embodiment shown in the drawing.

DESCRIPTION OF THE PREFERRED EMBODIMENTS

Figure 1:
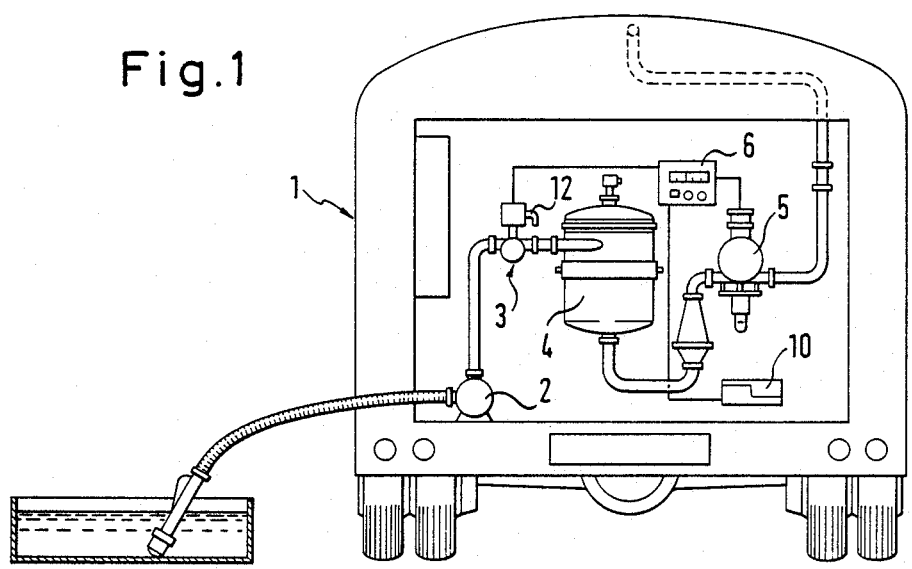
FIG. 1 is a schematic of a flow-meter system on a milk-collecting vehicle, where this system is the object of the invention.

As shown by FIG. 1, a flow-meter system is mounted on a milk-collecting truck 1, this system comprising in the direction of operation a self-priming pump 2, a pulse-controlled sampling device 3, an air separator 4 and a flowmeter 5 with a pulse generator and a display 6.

A computer (not shown in FIG. 1) is provided in the display 6 and controls, among its other functions, the sampling device 3.

Figure 2:
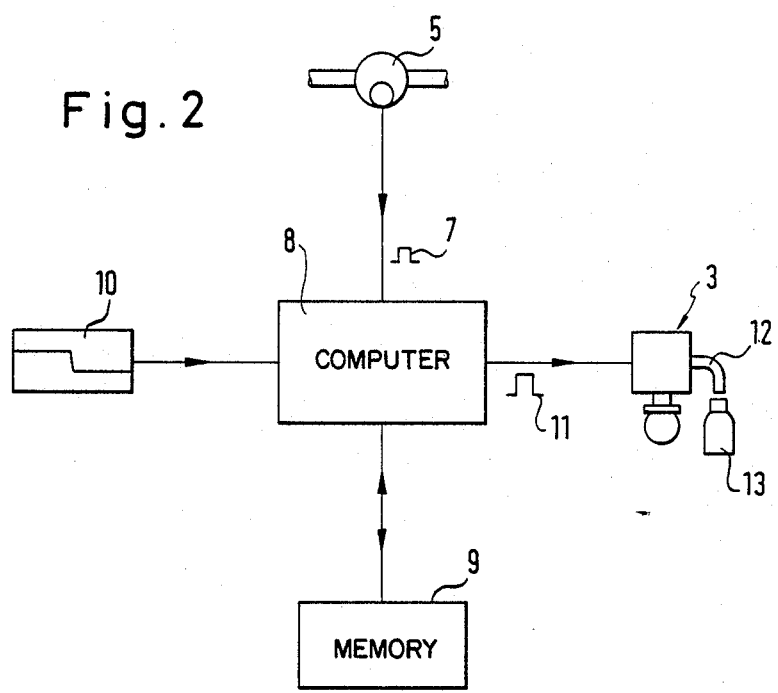
FIG. 2 is a circuit block diagram of an illustrative embodiment of the system of the invention, allowing the withdrawal of equal quantities of samples regardless of the particular quantity delivered.

FIG. 2 shows the particular conditions. The flowmeter 5 emits pulses 7 inherent in its design to the computer 8 which is connected to the memory 9 storing the quantities of milk delivered the particular day before by the suppliers. The memory 9 further contains supplier data such as their numbers or the like, whereby correlation is possible.

Such a correlation takes place in the computer 8 when supplier data—preferably supplier numbers—are fed by the input unit 10, which may be a card reader or the like, to the memory 8.

The computer 8 emits pulses 11 to the sampling device 3, the number of pulses being rigorously predetermined and illustratively being 20 for all quantities delivered. Accordingly the quantity per pulse will vary with difference delivery quantities and is ascertained in the computer 8 by the above formula. The pulses 11 are emitted on the basis of this computation and therefore will be distributed equally across the flow of a delivered quantity.

In the sampling device 3, the pulses 11 each time control the dischage of a specified amount of sample which may be from 1 to 3 ml/pulse. This amount is delivered through the discharge segment 12 into a sample withdrawing vessel 13. As the number of pulses 11 is just as predetermined as the amount of sample delivered by the sampling device 3, the filling of the container 13 can be kept nearly constant.

The pulses 7, which are far more numerous, are counted in the memory 8 independently from those above in order to display the particular flow quantity. They are also summed in the computer in order to trigger a pulse 11 fed to the sampling device 3 whenever the value of delivery-quantity/pulse computed by the above formula is being reached.

After reading-in the supplier-data, for instance a supplier number, by means of a coded card and the input unit 10, the associated previous-day quantity is fetched inside the computer 8 from the memory 9 and associated to the supplier number. The pulses 11 then are emitted on the basis of the previous-day quantity, while at the same time the new quantity being delivered is separately recorded.

Figure 3:
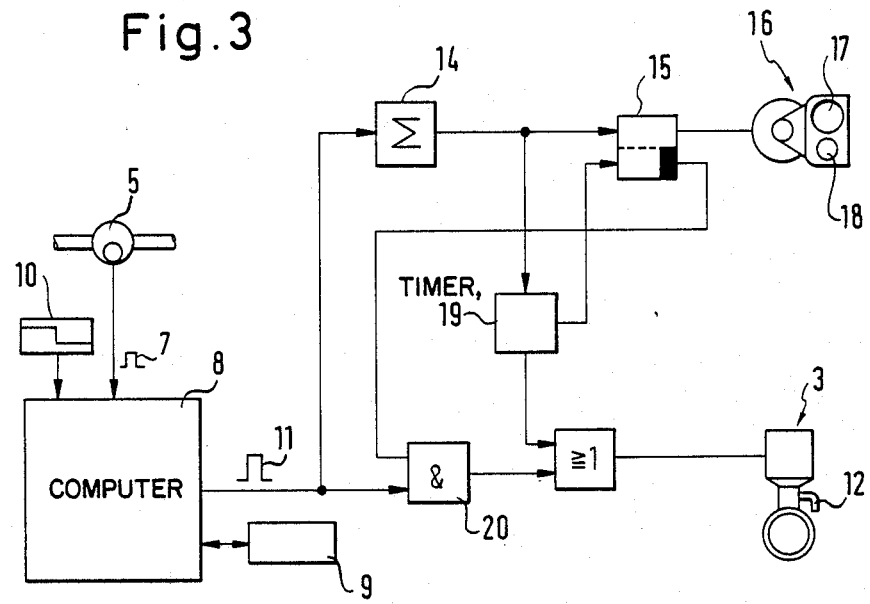
FIG. 3 shows the system of FIG. 2 supplemented by a further sampling-device design.

FIG. 3 is a circuit block diagram of a complemented system making it possible to withdraw additional samples in one step, for instance to ascertain the milk's bacteriological condition. This sample withdrawal preferably shall take place after half the pulses 11 have been emitted. To that end an adder 14 is provided which through a memory 15 drives a sample desk 16 which in the embodiment shown is equipped with two receiving openings 17 and 18 accepting different sample containers. The adder 14 sums the pulses 11 from the computer 8 and drives the sample desk 16 the moment the predetermined half number of pulse is being reached. Both the memory 15 and the sampling device 3 are fed from a timer 19; the memory also is connected through an AND gate to the sampling device 3.

This system allows switching the sample desk 16, each time one of the openings 17 and 18 moving underneath the discharge segment 12 of the sampling device 3.

Figure 4:
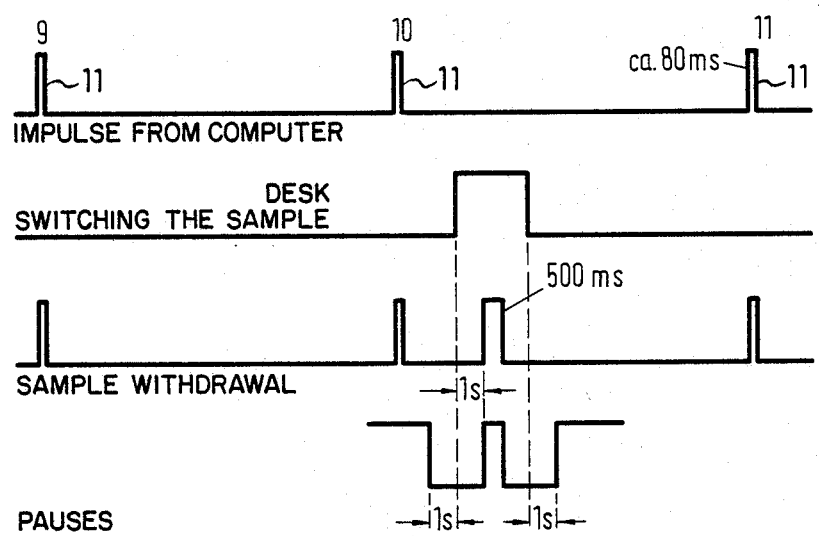
FIG. 4 is the time-plot for the additional sample withdrawal.

FIG. 4 shows the switching plot for the sample desk 16 and for turningon the sampling device 3.

As shown by FIG. 4, the pulses 11 are emitted from the computer 8 in equidistant intervals and in accordance with the second-last line they open the sampling device 3 for a brief time. As shown in the 2nd line of FIG. 4, the sample desk 16 is switched over for about 2.5 s in such a manner that the sample can be removed to determine the milk's bacteriological condition by the associated container being pivoted underneath the discharge segment 12 of the sampling device 3. During the switched-over state and within this time, the additional sample is withdrawn as shown by the third line and thereupon the brief sample withdrawal to ascertain the milk ingredients is continued.

The last line in FIG. 4 illustrates a pause during which both the sample withdrawal is blocked and the switching of the sample desk is delayed. The purpose is to prevent any sample withdrawal from beginning before the sample desk is fully switched or from proceeding during the return of the sample desk.

Figure 5:
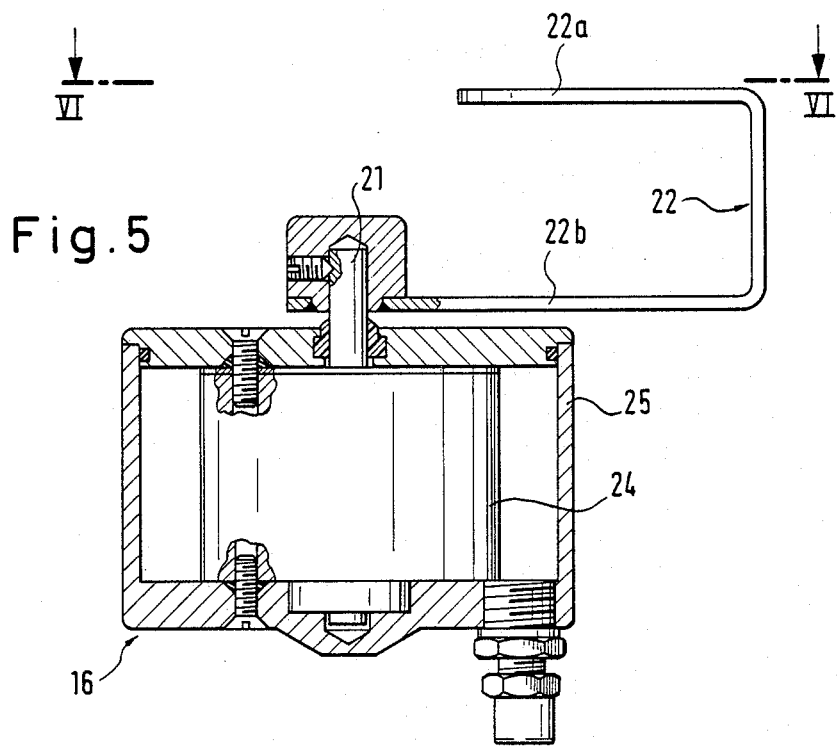
FIG. 5 is a sectional sideview of a switchable sample desk for the system of FIG. 3.
Figure 6:
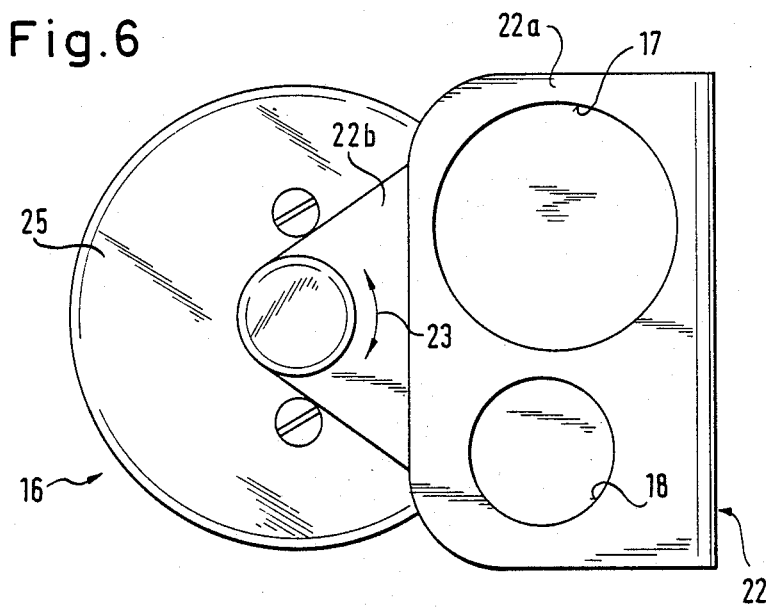
FIG. 6 is the view VI—VI of FIG. 5.

FIGS. 5 and 6 show an embodiment of the switchable sample desk. FIG. 5 is a sectional sideview of the details of the sample desk. In the embodiment shown, the sample desk 16 is equipped with a rotary magnet of which the case 19 is shown in FIG. 5. The rotary magnet is located within an outer housing 20. The core shaft of the rotary magnet is denoted by 21 and is connected to a U-shaped plate 22 of which the two legs 22a and 22b are horizontal the upper free leg 22a is provided with the two openings 17 and 18 (FIG. 6) to receive the sample container. The lower leg 22b is connected the core shaft 21 of the rotary magnet.

The sample desk 16 made of plate 22 therefore can be pivoted in the direction of the arrow 23 (FIG. 6); a limit stop (not shown) for the angular displacement is provided.

We claim:

1. A flow-meter system for milk-collecting vehicles comprising in sequential arrangement in an operational direction a pump, a pulse-controlled sampling device, an air separator and a flow-meter with pulse generator and display and a computer provided in said display for analysis, wherein said computer has means for storing the value of a given quantity of milk delivered the day before by the suppliers and said values are correlated to a particular supplier, a given number of pulses are assigned to all previous-day quantities by said computer, said pulses having a quantity-dependent pulse-train computed from said values and released by said flow-meter, whereby different previous-day quantities correspond to different delivered-quantity/pulses and where said pulses (11) drive said sampling device (3).

2. The system of claim 1, wherein a quotient of the previous-day quantity to amount of sample is formed in said computer (8) which thereupon determines the delivered quantity per pulse from the following relation:

$$V_1 = V_V P_1 / P$$

where
$V_1$ = delivered-quantity/pulse
$V_V$ = previous-day quantity
$P$ = amount of sample
$P_1$ = amount-of-sample/pulse.

3. The system of claim 23, wherein said pulses from said flow-meter (5) are added in said computer (8) in order that, when a given computed value is reached, said pulse (11) driving said sampling device (3) is transmitted and a given amount of sample is taken.

4. The system of claim 3, wherein a given supplier number or other supplier data is fed by means of an input unit (10) to said computer (8), whereupon said given quantity delivered the day before is correlated to said supplier and whereby the resulting delivered-quantity/pulse is computed, for delivery acceptance.

5. The system of claim 4, wherein 20 pulses are provided for said value of said given quantity delivered the day before.

6. The system of claim 5, wherein a value for the quantity estimated from the actual conditions is fed into said computer.

7. The system of claim 6, wherein following a given number of pulses driving said sampling device (3), said sampling device (3) is driven in one step to withdraw a predetermined, additional amount of sample.

8. The system of claim 7, wherein said additional amount of sample corresponds approximately to half said given amount of sample.

9. The system of claim 8, wherein a sample desk (16) switchable between first sample containers for the ingredients and for second sample containers for sampling bacteriological conditions and holding both containers associated with said sampling device (3).

10. The system of claim 9, wherein said sample desk (16) is in a rest position, and said first sample containers for determining the ingredients are associated with a discharge segment (12) of a valve of said sampling device (3).

11. The system of claim 10, wherein following a half of a pulse number, said sample desk (16) is switched to a position in which said discharge segment (12) is associated with said second container receiving a sample for determining the milk's bacteriological condition.

12. The system of claim 11, wherein following withdrawal of said predetermined, additional sample amount, said sample desk (16) is switched back into its initial position wherein sampling to determine ingredients is then continued.

13. The system of claim 12, wherein an adder (14) is provided for switching said sample desk, which sums the pulses from said computer (8) and feeds a memory (15) and by means of said memory drives said sample desk (16) the moment said predetermined half number of pulses (11) has been reached.

14. The system of claim 13, wherein said switching of said sample desk (16) takes place by means of a rotary magnet driven by said memory (15), a valve of the sampling device (3) being opened following switching by means of a timer (19) and a logic.

15. The system of claim 14, wherein said timer (19) is connected with said memory (15) and said sampling device (3) whereby sample withdrawal takes place at a delay of about 1 second after said sample desk (16) has been switched.

16. The system of claim 15, wherein a spring implements return of said sample desk (16).

17. The system of claim 16, wherein said timer (19) also shuts down said rotary magnet.

18. The system of claim 17, wherein said switching and return of said sample desk (16) is implemented by limit switches.

19. The system of claim 18, wherein said sample desk consists of a U-shaped plate (22) of which upper and lower legs (22a, 22b) are horizontal, said upper leg (22a) being provided with two openings (17, 18) to receive said sample containers.

20. The system of claim 19, wherein said lower leg (22b) is connected to a shaft (21) of the core of said rotary magnet.

21. The system of claim 20, wherein a limitation on the angular displacement of said sample desk (16) is provided.

* * * * *